US00PP17954P2

(12) United States Plant Patent
Olesen

(10) Patent No.: US PP17,954 P2
(45) Date of Patent: Aug. 28, 2007

(54) MINIATURE ROSE PLANT NAMED 'POULTY007'

(50) Latin Name: ***Rosa* hybrid**
Varietal Denomination: Poulty007

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 19 days.

(21) Appl. No.: 11/360,802

(22) Filed: Feb. 22, 2006

(51) Int. Cl.
*A01H 5/00* (2006.01)

(52) U.S. Cl. ..... Plt./117

(58) Field of Classification Search ..... Plt./117, Plt./118

See application file for complete search history.

*Primary Examiner*—Kent Bell
*Assistant Examiner*—June Hwu

(57) ABSTRACT

A new miniature rose plant that has abundant, white flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty007'.

SUMMARY OF THE INVENTION

The present invention constitutes a new and distinct variety of miniature rose plant which originated from a controlled crossing between the female seed parent, an unpatented variety named 'Menuet Femini', and the male pollen parent, an unnamed seedling by the same inventor.

The two parents were crossed during the summer of 2000 and the resulting seeds were planted in a controlled environment in Fredensborg, Denmark. The new variety, named 'Poulty007', originated as a single seedling from the stated cross.

The new variety may be distinguished from its female seed parent primarily by flower color and growth habit. The general tonality of flower color for the new variety 'Poulty007' is more pure white. 'Poulty007' is also more compact than the original seed parent variety.

The new variety may be distinguished from its male pollen parent by the following combination of characteristics:

1. 'Poulty007' exhibits more flowers per flowering stem.
2. 'Poulty007' plants are more compact than the pollen parent.

The objective of the hybridization of this rose variety for commercial culture was to create a new and distinct variety with unique qualities, such as:

1. Uniform and abundant white flowers;
2. Compact growth, suitable for 8–10 cm pot culture;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'Poulty007' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty007' was selected by the inventor as a single plant from the progeny of the hybridization in 2000.

Asexual reproduction of 'Poulty007' by cuttings and traditional budding was first done by Mogens N. Olesen in the nursery in Fredensborg, Denmark in April 2001. This initial and other subsequent propagations conducted in controlled environments have demonstrated that the characteristics of 'Poulty007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulty007'. Specifically illustrated in the drawing:

FIG. 1.1; Flower buds at various stages of development;

FIG. 1.2; Cluster of open flowers on single flowering stem;

FIG. 1.3; Flower reproductive parts with sepals, detached;

FIG. 1.4; Petals, detached;

FIG. 1.5; Bare stem exhibiting prickles;

FIG. 1.6; Mature leaves; and

FIG. 1.7; Juvenile leaves.

DETAILED DESCRIPTION OF THE VARIETY

The following is a description of 'Poulty007', as observed in its growth in a glasshouse in Fredensborg, Denmark. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulra015', U.S. Plant Pat. No. 14,309, are compared to 'Poulty007' in Chart 1.

CHART 1

| | 'Poulty007' | 'Poulra015' |
|---|---|---|
| Petalage: | 65 to 70 | 15 |
| Flower Diameter: | 50 to 60 mm | 50 to 55 min |
| General Tonality of Flower Color: | White 155A to Yellow 4D | Yellow 11D |

FLOWER AND FLOWER BUD

Blooming habit: Continuous.

Flower bud:

*Size.*—Upon opening, 28 to 31 mm in length from base of receptacle to end of bud. 12 mm in diameter.

*Bud form.*—Ovate.

*Bud color.*—As sepals unfold, petals are Yellow Group 4D.

*Sepals.*—Upper Surface: Color: Yellow-Green Group 146A to 147A. Texture: Smooth and pubescent. Lower Surface: Color: Yellow Green Group 146A. Texture: Smooth with few stipitate glands and light pubescence. Shape: Apex: Cirrhose. Base: Flat at union with receptacle. Margins: Margins have medium foliaceous appendages on three of the five sepals. Size: 30 mm long by 8 mm wide.

*Receptacle.*—Surface Texture: Smooth. Shape: Funnel shaped to urn-shaped. Size: 13 mm (h)×10 mm (w). Color: Yellow Green Group 144A. Anthocyanin: None observed.

*Pedicel.*—Surface: Somewhat rough with stipitate glands and small prickles. Length: 15 to 20 mm. Diameter: Normally 3 mm. Color: Yellow-Green Group 146B. Strength: Erect, moderately strong.

*Borne.*—Singly and in small clusters comprising 3 to 4 flower buds per flowering stem.

Flower bloom:

*Fragrance.*—Very light floral scent.

*Duration.*—As a pot plant, flowers last from 15 to 18 days. Petals generally do not fall away cleanly from the plant after flowers have matured.

*Size.*—Individual flowers are 50 to 60 mm in diameter. Average flower depth is 20 to 25 mm.

*Form.*—Flowers take shape very orderly. Initially flowers exhibit a classic hybrid tea rose shape. As flower mature, the form resembles an imbricated rosette with many overlapping petals.

*Shape of flower, side view.*—Upon opening, the upper portion is convex. The lower portion is flattened convex. After opening, the upper portion is convex. The lower portion is concave.

*Petalage.*—There are normally 65 to 70 petals, 30 to 35 of which are underdeveloped petaloids.

Color:

*Upon opening, petals.*—Outermost petals: Upper Surface: Yellow Group 4D with very a small basal spot of Yellow Group 4C. Lower Surface: Yellow Group 4D with very a small basal spot of Yellow Group 4C. Innermost petals: Upper Surface: Yellow Group 4D with very a small basal spot of Yellow Group 4C. Lower Surface: Yellow Group 4D with very a small basal spot of Yellow Group 4C.

*After opening, petals.*—Outermost petals: Upper Surface: White Group 155A with light intonations of Green-Yellow Group 157A. Lower Surface: White Group 155A with light intonations of Green-Yellow Group 157A. Innermost petals: Upper Surface: White Group 155A with light intonations of Green-Yellow Group 157A. Lower Surface: White Group 155A with light intonations of Green-Yellow Group 157A.

*After opening, basal petal spots.*—No distinctive coloration at petal base observed.

General tonality: On open flower White Group 155A to Yellow Group 4D. As flowers mature, general tonality is White Group 155A to Yellow Group 4D with intonations of Yellow-Green Group 145D.

Petals:

*Petal reflex.*—Strong reflexing at the petal margins.

*Petal margin.*—Entire with medium undulations.

*Shape.*—Generally narrow elliptical. Base: Acute. Apex: Rounded.

*Size.*—Petal size varies. Outer petals 25 to 30 mm (l)×23 to 27 mm (w). Inner petals 22 mm (l)×15 mm (w).

*Thickness.*—Average.

Petaloids:

*Quantity.*—On average, 30 to 35.

*Size.*—10 to 20 mm long; 5 mm wide.

*Shape.*—Apex is acute. Base is acute. Generally the petaloids are irregular and asymmetrical.

*Color.*—White Group 155A with light intonations of Green-Yellow Group 157A.

Reproductive organs:

*Pollen.*—None observed.

*Anthers.*—Size: 2 mm long. Color: Yellow Group 7D. Quantity: 30 to 35.

*Filaments.*—Color: White Group 155A. Length: 8 mm.

*Pistils.*—Length: 3 mm long. Quantity: 45 to 50.

*Stigmas.*—Slightly inferior relative to the length of the filaments and the height of the anthers. Color: Greyed-Yellow Group 160D.

*Styles.*—Color: Greyed-Yellow Group 160C.

*Seed formation.*—Not observed.

PLANT

Plant growth: Moderate upright to bushy. Very compact. When grown as a 8–11 cm pot plant on its own roots, the average height of the plant itself is 15 cm and the average width is 15 cm.

Stems:

*Color.*—Young wood: Yellow-Green Group 144A. Older wood: Green Group 138B.

*Internodal distance.*—On mature canes, 20 to 25 mm.

*Length of stems.*—On average, canes are 10 to 13 cm from the base of the stem to the flowering portion.

*Diameter.*—Normally 3.5 mm.

*Surface texture.*—Young wood: Smooth. Older wood: Somewhat rough with small prickles.

Prickles:

*Incidence.*—10 to 12 prickles per 10 cm of stem.

*Size.*—Average length: 6 mm.

*Color.*—Juvenile prickles are Greyed-Red Group 180C. Mature prickles are Greyed-Red Group 180C.

*Shape.*—Upper side: Flat. Lower side: Deeply concave.

Plant foliage: Normal number of leaflets on normal leaves in middle of the stem: 5 leaflets.

*Compound leaf size.*—80 to 90 mm (l)×55 to 65 mm (w).

*Quantity.*—4 to 5 leaves per 10 cm of stem.

*Color.*—Juvenile foliage: Upper Leaf Surface: Yellow-Green Group 146A with anthocyanic pigments of Greyed-Red Group 182B on the margins. Lower Leaf Surface: Yellow-Green Group 147C with anthocyanic intonations of Greyed-Red Group 182B generalized. Mature foliage: Upper Leaf Surface: Yellow-Green Group 147A. Lower Leaf Surface: Yellow-Green Group 147C to 148C.

Plant leaves and leaflets:

*Stipules.*—Size: 12 mm (l)×2 mm (w). Shape: Linear, slightly broad based with outward extending apecies. Margins: Finely serrated with stipitate glands. Color: Yellow-Green Group 146A.

*Petiole.*—Length: 15 to 20 mm. Upper surface: Color: Yellow-Green Group 146A with anthocyanic pigments of Greyed-Purple 183A. Observations: Numerous stipitate glands. Lower surface: Color: Yellow-Green Group 146B. Observations: Few small prickles observed.

*Rachis.*—Size: 22 to 25 mm in length. Upper surface: Color: Yellow-Green Group 146A with strong anthocyanic pigments of Greyed-Purple 183A. Observations: Numerous stipitate glands. Lower surface: Color: Yellow-Green Group 146B. Observations: Few small prickles observed.

*Leaflet.*—Size: Normally 35 to 47 mm in length by 20 to 25 mm wide. Edge: Serrated. General Shape: Ovate. Apex Shape: Acute. Base Shape: Rounded. Texture: Smooth. Thickness: Average. Arrangement: Odd pinnate. Venation: Reticulate. Leaf Gloss: Matte finish.

Disease resistance: Average resistance to powdery and downy mildew, black spot, and *Botrytis* under normal growing conditions in Fredensborg, Denmark.

It is claimed:

1. A new and distinct variety of rose plant of the miniature class named 'Poulty007', substantially as illustrated and described herein, due to its abundant, white flowers, vigorous growth, compact habit, suitability for production from softwood cuttings in pots, and durable flowers and foliage that make the variety suitable for distribution in the floral industry.

* * * * *

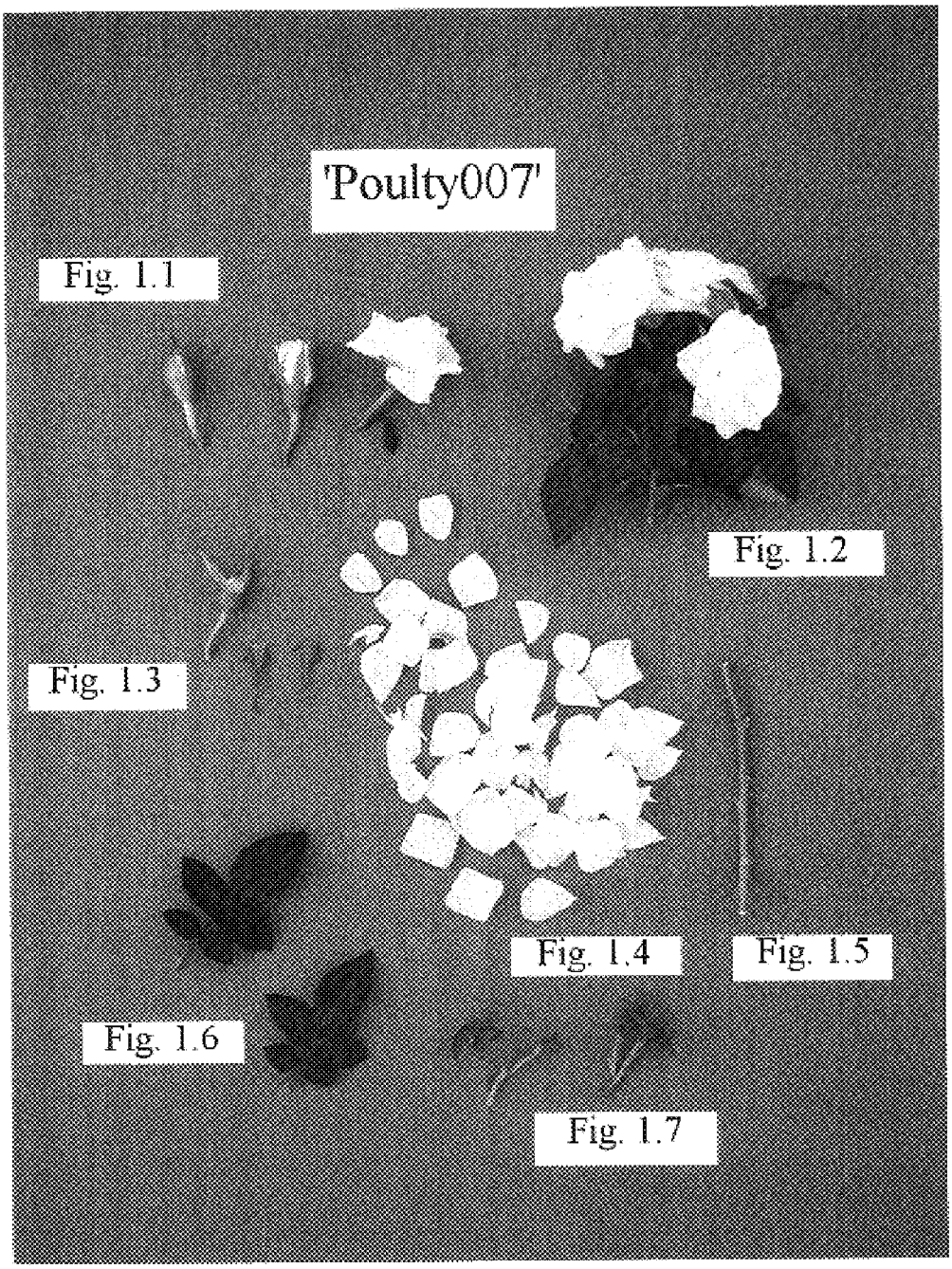
'Poulty007'
Fig. 1.1
Fig. 1.2
Fig. 1.3
Fig. 1.4
Fig. 1.5
Fig. 1.6
Fig. 1.7